(12) United States Patent
Lowder

(10) Patent No.: US 7,790,203 B2
(45) Date of Patent: Sep. 7, 2010

(54) COMPOSITION AND REGIMEN FOR THE TREATMENT OF HERPES SIMPLEX VIRUS, HERPES ZOSTER, AND HERPES GENITALIA EPIDERMAL HERPETIC LESIONS

(76) Inventor: Tom R. Lowder, P.O. Box 406, Elkins, AR (US) 72727

( * ) Notice: Subject to any disclaimer, the term of this patent is extended or adjusted under 35 U.S.C. 154(b) by 320 days.

(21) Appl. No.: 11/302,057

(22) Filed: Dec. 13, 2005

(65) Prior Publication Data

US 2007/0134320 A1 Jun. 14, 2007

(51) Int. Cl.
| | |
|---|---|
| A61K 33/00 | (2006.01) |
| A61K 33/30 | (2006.01) |
| A61K 33/04 | (2006.01) |
| A61K 33/06 | (2006.01) |
| A61K 9/48 | (2006.01) |
| A61K 9/20 | (2006.01) |
| A01N 59/16 | (2006.01) |
| A01N 59/02 | (2006.01) |
| A01N 59/06 | (2006.01) |

(52) U.S. Cl. ............... 424/643; 424/641; 424/451; 424/464; 424/682; 424/692; 424/709; 514/904; 514/934

(58) Field of Classification Search ............ None
See application file for complete search history.

(56) References Cited

U.S. PATENT DOCUMENTS

| | | | |
|---|---|---|---|
| 4,522,814 A | 6/1985 | Nonomura et al. | |
| 4,661,354 A * | 4/1987 | Finnerty | 424/642 |
| 5,034,382 A | 7/1991 | Osswald | |
| 5,081,010 A | 1/1992 | Cummins et al. | |
| 5,124,245 A | 6/1992 | Cummins et al. | |
| 5,132,205 A | 7/1992 | Pronovost et al. | |
| 5,210,039 A | 5/1993 | Cummins et al. | |
| 5,403,826 A | 4/1995 | Cope et al. | |
| 5,834,443 A | 11/1998 | Masiello | |
| 5,869,084 A * | 2/1999 | Paradissis et al. | 424/439 |
| 5,976,568 A * | 11/1999 | Riley | 424/451 |
| 6,013,265 A | 1/2000 | Aurelian | |
| 6,015,566 A | 1/2000 | Golubev et al. | |
| 6,054,131 A | 4/2000 | Aurelian | |
| 6,074,649 A | 6/2000 | Audonnet et al. | |
| 6,153,226 A | 11/2000 | Vachy et al. | |
| 6,193,984 B1 | 2/2001 | Ghiasi et al. | |
| 6,207,168 B1 | 3/2001 | Aurelian | |
| 6,284,289 B1 | 9/2001 | Van den Berghe | |
| 6,455,061 B2 | 9/2002 | Richardson et al. | |
| 6,488,936 B1 | 12/2002 | Mishkin et al. | |
| 6,733,797 B1 * | 5/2004 | Summers | 424/728 |
| 6,914,073 B2 * | 7/2005 | Boulos et al. | 514/458 |
| 6,936,255 B1 | 8/2005 | Wettendorff | |
| 7,025,996 B1 * | 4/2006 | Miladinov et al. | 424/725 |

OTHER PUBLICATIONS

Rudnic et al. Oral Solid Dosage Forms; Remingtons Pharmaceutical Sciences 1990 18th Ed chapter 89.*
Swain Pharmaceutical and Medical Packaging News Magazine 1999 pp. 1-4).*
Nutrition Data Garlic [online] retrieved from the internet on May 7, 2008; retrieved from http://www.nutritiondata.com/facts-C00001-01c20dS.html?print=true; pp. 4.*
Eby et al. (Medical Hypothesis 1985, 17(2), 157-65).*

* cited by examiner

*Primary Examiner*—Ernst V Arnold
(74) *Attorney, Agent, or Firm*—Bliss McGlynn, P.C.

(57) ABSTRACT

A composition and treatment regimen for the amelioration of epidermal herpetic lesions caused by Herpes Simplex Virus (HSV-1) symptoms, Herpes Zoster, and Herpes Genitalia. The treatment includes a regimen of oral administration of a composition including from about 15 to 50 mg of zinc sulfate, from about 5 to 20 mg of magnesium sulfate, from about 15 to 60 mg of thiamin, from about 10 to 30 mg of riboflavin, from about 4 mg to 12 mg of pyridoxine hydrochloride, from about 300 to 1000 mg of ascorbic acid, from about 90 to 300 mg of niacin, and from about 20 to 70 mg of pantothenic acid. The composition and regimen may optionally include an efficacious amount of an amino acid, and preferably about 500 mg of lysine.

15 Claims, No Drawings

COMPOSITION AND REGIMEN FOR THE TREATMENT OF HERPES SIMPLEX VIRUS, HERPES ZOSTER, AND HERPES GENITALIA EPIDERMAL HERPETIC LESIONS

BACKGROUND OF THE INVENTION

1. Field of the Invention

The present invention relates generally to a composition and a regimen for the treatment of epidermal herpetic lesions caused by Herpes Simplex Virus (HSV-1), Herpes Zoster, or Herpes Genitalia.

2. Description of the Related Art

Antiviral agents, such as Zovirax, are somewhat effective in the treatment of epidermal herpetic lesions caused by Herpes Simplex Virus (HSV-1). However, it has been found that they increase the potential for contact spread of the virus because the user must apply these compositions directly to the lesions. This direct contact may spread the virus to the hand of the user, and thereby spread the virus to other parts of the body. Topical application, without extreme caution, may be a common mode of spreading the viral infection. Any contact between the cold sore and a finger, whether it has been used to apply a topical treatment or otherwise, becomes a source to spread the virus. Although oral administrations of antiviral agents for systemic treatment are valuable additions to the treatment modalities currently used for epidermal herpetic lesions, the possibilities for side effects are always a concern.

In addition, it is also known that zinc compounds, particularly zinc sulfate containing compounds, may have some therapeutic application to Herpes Simplex Virus, but these compositions are usually applied topically, and may have the same potentials to spread the virus as previously discussed.

It is, therefore, desirable to provide a modality for the oral administration of an anti-viral composition that is all natural, efficacious, easy to administer and without any side effects that may be seen in other orally administered treatments for epidermal herpetic lesions. Thus, there is a need in the art for a composition and regimen that meets these desires.

SUMMARY OF THE INVENTION

It is, therefore, one object of the present invention to provide a composition and treatment regimen to ameliorate the symptoms of epidermal herpetic lesions.

It is another object of the present invention to provide a composition and treatment regimen to ameliorate the symptoms of herpetic epidermal lesions caused by Herpes Simplex Virus (HSV-1) Herpes Zoster, and Herpes Genitalia virus.

It is yet another object of the present invention to provide a treatment for the amelioration of Herpes Simplex Virus (HVS-1) symptoms.

To achieve at least one of the foregoing objects, the present invention is a treatment to ameliorate the symptoms of herpetic lesions caused by Herpes Simplex Virus (HSV-1), Herpes Zoster and Herpes Genitalia, including a regimen of oral administration of a composition comprising:
 a) from about 15 to 50 mg of zinc sulfate, zinc oxide, and mixtures thereof;
 b) from about 5 to 25 mg of magnesium sulfate, magnesium oxide, and mixtures thereof;
 c) from about 15 to 60 mg of thiamin;
 d) from about 10 to 30 mg of riboflavin;
 e) from about 4 mg to 12 mg of pyridoxine hydrochloride;
 f) from about 300 to 1000 mg of ascorbic acid;
 g) from about 90 to 300 mg of niacin; and
 h) from about 20 to 70 mg of pantothenic acid; and;
 i) optionally an efficacious amount of an amino acid selected from the group consisting of lysine, taurine, L-methionine, L-glutamine, L-arginine, L-carnitine, and mixtures thereof, and preferably about 500 mg of lysine.

The treatment regimen is conducted over a seven-day period wherein varying loading dosages are ingested orally over the seven-day treatment period.

One advantage of the present invention is that a composition and treatment regimen is provided to ameliorate the symptoms of epidermal herpetic lesions. Another advantage of the present invention is that oral administration of the composition of the present invention in the varying dosages as disclosed herein greatly decreases the discomforts and symptoms of epidermal herpetic lesions that accompanying an outbreak of Herpes Simplex Virus (HVS-1), Herpes Zoster, and Herpes Genitalia.

Other objects, features, and advantages of the present invention will be readily appreciated, as the same becomes better understood, after reading the subsequent description.

DESCRIPTION OF THE PREFERRED EMBODIMENT(S)

The present invention is a treatment regimen of the amelioration of Herpes Zoster, Herpes Genitalia, and Herpes Simplex Virus (HVS-1) symptoms, specifically, herpetic epidermal lesions that accompany an outbreak of these Herpes Viruses. These herpetic epidermal lesions commonly known as "cold sores" or "fever blisters" are painful, uncomfortable, embarrassing and unsightly to the sufferers.

The present invention is a composition when ingested over a treatment period of seven days in varying dosages as described herein, greatly reduces the symptoms of herpetic epidermal lesions and has been determined to greatly reduce recurrent outbreaks of the viruses and the attendant epidermal herpetic lesions.

The composition of the present invention is comprised of:
 a) from about 15 to 50 mg of zinc sulfate, zinc oxide and mixtures thereof;
 b) from about 5 to 25 mg of magnesium sulfate, magnesium oxide and mixtures thereof;
 c) from about 15 to 60 mg of thiamin;
 d) from about 10 to 30 mg of riboflavin;
 e) from about 4 mg to 12 mg of pyridoxine hydrochloride;
 f) from about 300 to 1000 mg of ascorbic acid;
 g) from about 90 to 300 mg of niacin; and
 h) from about 20 to 70 mg of pantothenic acid; and
 i) optionally an efficacious amount of an amino acid selected from the group consisting of lysine, taurine, L-methionine, L-glutamine, L-arginine, L-carnitine, and mixtures thereof, and preferably about 500 mg of lysine.

The composition is compounded into an orally ingestible form by the addition of an efficacious amount of mononitrate, sodium lauryl, pyridoxine hydrochloride, titanium dioxide, talc, stearic acid, vegetable acetoglycerides, soybean oil, microcrystalline cellulose, gelatin, and may further include a colorant, such as caramel color and flavoring, such as ethyl vanillin. The composition may be compounded into a tablet form, or more preferably into a capsule form, and placed in a blister pack that follows the regimen of the present invention to permit a user to take the recommended dosages to treat the outbreak of herpetic epidermal lesions that are caused by herpes viruses, specifically herpes simplex (HVS-1), herpes zoster and herpes genitalia viruses. In this regard, it is further contemplated that each dose would be in its own blister package, and may be labeled with an indication as to which day that particular dose was to be consumed within the treatment regimen.

The treatment regimen for the amelioration of Herpes Simplex Virus (HSV-1), Herpes Zoster and Herpes Genitalia symptoms, mainly epidermal herpetic lesions attended with an outbreak of Herpes Simplex Virus (HSV-1), Herpes Zoster, or Herpes Genitalia includes ingesting varying loading dosages of the composition on a daily basis over a recommended treatment period. The recommended treatment period is about seven days that includes on a first day, of ingesting from a first package:
   a) from about 30 to 50 mg of zinc sulfate;
   b) from about 15 to 25 mg of magnesium sulfate;
   c) from about 45 to 60 mg of thiamin;
   d) from about 25 to 30 mg of riboflavin;
   e) from about 8 to 12 mg of pyridoxine hydrochloride;
   f) from about 900 to 1000 mg of ascorbic acid;
   g) from about 270 to 300 mg of niacin; and
   h) from about 65-70 mg of pantothenic acid.

On each of a second and third day, the regimen further includes ingesting from a second and third package:
   a) from about 20 to 30 mg of zinc sulfate;
   b) from about 10 to 15 mg of magnesium sulfate;
   c) from about 30 to 40 mg of thiamin;
   d) from about 15 to 20 mg of riboflavin;
   e) from about 8 to 12 mg of pyridoxine Hydrochloride;
   f) from about 600 to 1000 mg of ascorbic acid;
   g) from about 180 to 200 mg of niacin; and
   h) from about 40 to 65 mg of pantothenic acid.

On each of a fourth through a seventh day, the regimen includes ingesting from a fourth, fifth, sixth and seventh package:
   a) from about 15 to 20 mg of zinc sulfate;
   b) from about 5 to 10 mg of magnesium sulfate;
   c) from about 15 to 20 mg of thiamin;
   d) from about 10 to 15 mg of riboflavin;
   e) from about 4 to 8 mg of pyridoxine hydrochloride;
   f) from about 300 to 600 mg of ascorbic acid;
   g) from about 90 to 180 mg of niacin; and
   h) from about 20 to 40 mg of pantothenic acid.

It has been found that by following the regimen as described herein, herpetic epidermal lesions caused by Herpes Simplex Virus (HSV-1), Herpes Zoster or Herpes Genitalia are greatly reduced and the lesions dry quicker, do not spread as quickly, and are less painful than otherwise might be experienced if no treatment at all was undertaken by the sufferer.

The composition and regimen of the present invention may also optionally include an efficacious amount of amino acids selected from the group consisting of lysine, taurine, L-methionine, L-glutamine, L-arginine, L-carnitine, and mixtures thereof. The amino acids may be present in an amount of about 500 mg, and lysine is the amino acid of choice.

The composition and treatment regimen of the present invention may also include Folic Acid, Selenium, Copper, Chromium, Manganese and its sulfate, Molybdenum, and an antioxidant. Antioxidants that are particularly attractive in this regard are vitamins such as Vitamin E.

The treatment regimen can be presented in tablet form, or more preferably in capsule form, in blister packages wherein each blister package is labeled to correspond to the day of treatment within the regimen as described herein. Such a packaging would offer the sufferer a convenient and easy to follow routine for the treatment of the herpetic epidermal lesions caused by Herpes Simplex Virus (HSV-1), Herpes Zoster, and Herpes Genitalia.

The following examples are included to illustrate various aspects of the present invention and are not to be construed as limiting the description or the scope of the invention. Rather they are included merely to illustrate the efficacious nature of the regimen and composition of the present invention.

EXAMPLES

In each example, each of the patients was started with a dosage that was approximated for their body weights. For the adult males the average initial loading dosage for days 1 and 2 was:

| | |
|---|---|
| Vitamin C | 900 mg |
| Thiamin | 54 mg |
| Niacin | 285 mg |
| Pantothenic acid | 65 mg |
| Magnesium | 19.2 mg |
| Zinc | 48 mg |
| Riboflavin | 30 mg |
| Vitamin B6 | 15 mg |

Reduced loading average dosage for adult males for days 3 and 4 was:

| | |
|---|---|
| Vitamin C | 600 mg |
| Thiamin | 36 mg |
| Niacin | 200 mg |
| Pantothenic acid | 44 mg |
| Magnesium | 13 mg |
| Zinc | 30 mg |
| Riboflavin | 20 mg |
| Vitamin B6 | 10 mg |

Daily average dosage for adult males after the initial and decreased loading dosages for days 5, 6, and 7 was:

| | |
|---|---|
| Vitamin C | 200 mg |
| Thiamin | 12 mg |
| Niacin | 100 mg |
| Pantothenic acid | 22 mg |
| Magnesium | 6 mg |
| Zinc | 15 mg |
| Riboflavin | 10 mg |
| Vitamin B6 | 5 mg |

The average Initial Loading Dosage for adult females was:

| | |
|---|---|
| Vitamin C | 600 mg |
| Thiamin | 36 mg |
| Niacin | 200 mg |
| Pantothenic acid | 44 mg |
| Magnesium | 13 mg |
| Zinc | 30 mg |
| Riboflavin | 20 mg |
| Vitamin B6 | 10 mg |

The females on average were given the same loading dosage for 2-3 days (since the initial loading dosage for the females was reduced already in comparison to the males, it was not reduced further)

The daily dosage for females to complete the 7-day coverage was the same as for the males:

| | |
|---|---|
| Vitamin C | 200 mg |
| Thiamin | 12 mg |
| Niacin | 100 mg |
| Pantothenic acid | 22 mg |
| Magnesium | 6 mg |
| Zinc | 15 mg |
| Riboflavin | 10 mg |
| Vitamin B6 | 5 mg |

The child in the examples was given one-half (½) of the average dosage for adult females.

Example 1

Test Subject TRL was a 60 Year Old Caucasian male

History: Very active outdoor enthusiast engaging in both recreational and work related activities in the direct sunshine and extreme ranges of temperature. Patient reported a history of recurrent Herpes Simplex lesions at the angle of his lip on the left. Lesions were described as starting with a stinging sensation for 12 to 24 hours followed by blister formation which would rupture within 24 hours leaving an open weepy sore. Due to the location of the lesions at the corner of the mouth where they are subject to stretching and cracking, the sore frequently took 2-3 weeks to heal. Recurrent lesions were experienced approximately once per month and increased to three or more per month dependant on the duration and intensity of his exposure to sunshine. Patient also reported an increase of lesions and the susceptibility to the lesions in direct relationship to the altitude at the time of exposure to sunshine (possibly related to the increased ultraviolet exposure). He reported that the recurrent episodes dated from childhood. Patient had sought treatment by both over the counter and prescription medications, both topically and orally administered including antivirals.

Treatment: The compounded formulation was administered to the patient as described in the patent application at the onset of the familiar stinging sensation at the onset of a herpetic lesion. The patient reported that within 3-4 hours the stinging sensation will cease and within 6-8 hours the area of the lesion will dry. The accompanying swelling will resolve entirely within hours or not occur at all, if the formulation is started at the very first indication of lesion formation.

Subsequent Observation and Treatment: Patient has been followed closely for over 12 months since the initial treatment. Patient has experienced no more than one episode of recurrent herpetic activity since the initial treatment. As soon as the patient recognized the symptoms of herpetic activity, a burning sensation and swelling, he would administer the recommended formulation. Patient has not experienced the sufficient development of a lesion to form an open sore during the observation period except for one occasion when traveling and the recommended treatment was not available until after the outbreak had developed into an open weepy sore. Upon obtaining the recommended formulation he initiated the treatment with the lesion being at the point of it an open sore. He noted that the lesion had dried and all pain ceased within 10-12 hours. The entire herpetic episode had been limited to less than 7 days even with the delayed application of the recommended treatment modality as compared to an average of his previous experiences of two weeks or more without treatment.

Example #2

Patient JCL—62 Year Old Caucasian male

History: Patient reported recurrent herpetic lesions since childhood occurring at two locations around his mouth, the vermillion border of the upper lip to the right of the mid-line and at the mid-line of the lower lip. Even relatively short exposures to sunshine on hot days would result in painful herpetic lesions. Patient had sought treatment by both over the counter and prescription medications, both topically and orally administered. No treatment had resulted in acceptable resolution of symptoms or prevention of reoccurrences. Episodes were reported to be occurring approximately 2 times per month.

Treatment: The compounded formulation was administered as described in the patent application at the onset of a herpetic lesion. He related that the lesion did not progress to the blister stage and was not discernable within 24 hours.

Subsequent Observation, Treatment and Prevention: The initial treatment was over 12 months ago. The patient was so encouraged by his initial response to the formulation that a routine of prevention regimen was initiated using a maintenance level of the formulation. Patient stated that prevention works well for him with the formulation. He has not experienced a herpetic lesion within the past 12 months (Note: The preventive regimen has consisted of taking a smaller quantity of the loading dosage twice weekly. If prolonged or intense exposure to the sun is anticipated, a loading dosage is taken the day prior to the anticipated exposure in addition to the biweekly dosages.)

Example #3

Patient JB, D.D.S.—a 52 Year Caucasian Male Practicing Restorative Dentist

History: Patient reported recurrent herpetic lesions in two locations on his lips, the vermillion border of the upper lip and the mid-line of the lower lip. He stated that he had been susceptible to herpetic lesions since childhood. The episodic outbreaks most frequently occurred after an exposure to the sunshine. Following the death of a loved one, the frequency of herpetic episodes increased dramatically and began to occur without exposure to sun. The frequency increased to an episode every other week accompanied by a considerable increase in both swelling and pain. The lesions seemed to him to be increasing in size and duration of activity. Upon administration of the recommended formulation several days after the onset of a herpetic episode, he experienced a much more rapid healing of the lesions in comparison to the healing of previous lesions that he had experienced.

Subsequent Observation, Treatment and Prevention: Patient has reported two herpetic lesions that reached the blister stage within the first 4 months following the initial treatment. Each of the two episodes occurred at times when he was without the prescribed formulation. Upon obtaining the formulation and taking it as prescribed, the lesions began to subside within 12-24 hours and dried rapidly compared to his previous experiences with herpetic lesions. He was able to prevent at least 4 other episodes of herpetic lesions from developing during that same period. He had not ever been able to control the outbreaks of lesions using OTC or prescription medications, both of which had been readily available to him as a dental practitioner. He stated that he now prescribes the formulation to patients presenting in his dental practice with histories of recurrent herpetic lesions.

Example #4

Patient JTM—29 Year Old Caucasian Female Orthodontic Chairside Assistant
History: Patient presented with a slight hint of swelling to the left of the mid-line of her lower lip. She described a sensation that felt as if she had, "busted my lip". As the member of a professional health care team, she correctly recognized it as the start of a herpetic lesion and sought treatment immediately.
Treatment: Patient initiated treatment with the recommended formulation. She reported that blister formation was prevented and that the painful sensation was gone within 12-15 hours. The area felt normal to her within 2-3 days. (Note: This was her first experience with a herpetic lesion. The initial exposure and infection with the Herpes Simples Virus ordinarily is usually a more painful and longer lasting episode than recurrent lesions at the same site. The patient has no antibodies to the virus prior to the initial infection. The fact that the lesion did not develop further may be an indication of the efficacy of the formulation and recommended treatment modality.)
Subsequent Observation, Treatment and Prevention: Her professional ability to recognize the onset of the infection coupled with the ready availability of the formulation enabled her to avoid a painful episode. This patient will be followed to determined if further episodes occur at the original site of infection.

Example #5

Patient BDP—30 Year Old Caucasian Female
History: Patient reported that she had suffered from recurrent episodes of herpetic lesions for as long as she could remember. Occurrences were at least once per month and frequently occurred 2-3 times per month. Most frequent sites of infection were the right corner of her mouth, the upper mid-line of the lip at the vermillion border, and the lower lip near the left corner, entirely within the lip and not reaching to the vermillion border. She further stated that the episodes were increasing in frequency and intensity. The lesions were also spreading to other sites around her mouth and bilateral inside her nose. Frequently episodes involved several sites at the same time. She stated that the most painful lesions were the ones that occurred inside of her nose. She reported that she had used both over the counter and prescription treatments including systemic antivirals. Her most dependable relief was provided by over the counter, topically applied 20% Benzocaine, Ziactin, which provided at least some pain relief, but did not diminish the length of time required for a lesion or lesions to heal. She reported that she and her daughter were on at least two separate occasions certain that they had transmitted the virus between each other.
Treatment: Patient started the formulation at the onset of the initial symptoms of a fever blister, which by that time had become both recognizable and predictable to her. She reported that the fever blister developed no further than the stage that it was at when she initiated the treatment. The area of the lesion was dried and without pain by the next morning.
Subsequent Observation, Treatment and Prevention: Patient has used the formulation as directed for over 12 months. She stated that if she feels the onset of a herpetic lesion, she starts taking the formulation as directed. The lesion or lesions immediately begin to dry and within 24 hours are asymptomatic and are not noticeable by other people.

Example #6

Patient SJW—7-½ Year Old Caucasian Female.
History: Both the patient and her mother had a significant history of episodic herpetic lesions in multiple sites of infection. On at least two occasions both the patient and her mother felt that they had transmitted the virus between themselves. The patient's mother started treatment with the prescribed formulation for her herpetic lesions and experienced such significant results that she inquired as to the availability of the same treatment for her daughter.
Treatment: Patient was 7-½ years of age when the formulation was first prescribed at a much reduced loading and treatment dosage. She was given one-half (½) of the loading dosage for an adult on the first day. The loading dosage was broken into 3 doses taken with meals. She was subsequently given one-half (½) of the treatment dose daily for 5 days with food. The lesion did not develop further and was beginning to dry within 12 hours.
Subsequent Observation, Treatment and Prevention: Patient has continued for over 12 months to use the reduced dosage as needed when she feels the initial onset of symptoms and has not had a fever blister progress beyond the initial burning or stinging sensation during that time frame.

Example #7

Patient: MavMcP—approx 50 Year Old Caucasian Female.
History: The patient was experiencing an initial occurrence of Herpes Zoster with no previous history of having had "Shingles". The formulation was prescribed and taken as directed. The patient reported through a third party that her response was significant and both the pain and duration of the infection were reduced. Due to an incomplete follow-up at this time, lack of direct patient interview and the fact that the patient was experiencing her first episode of "Shingles" (might have difficulty in assessing the degree of efficacy of a treatment modality without a basis for comparison), no conclusion may be drawn at this time. A complete patient follow-up will be forthcoming. However, the initial indication is that the patient at least felt that the formulation was helpful in the treatment of her malady. Due to the similarity of the herpes viruses, it would not be surprising if forthcoming studies will confirm the efficacy of the formulation in the treatment of Herpes Zoster (Shingles) and perhaps Chicken Pox.
Statement of Efficacy: As a practicing orthodontist, the patent applicant has prescribed the formulation to hundreds of patients and/or their parents and/or siblings. I have yet to have an individual for whom the formulation was prescribed, fail to report a very significant response in the frequency and/or diminished pain and duration of herpetic lesions. The efficacy of this formulation for the treatment of herpetic lesions exceeds by far that of any other medication of which the tester was familiar.
Mode of Action: Although the exact mode of action of the formulation is uncertain, all of the ingredients are known to be essential to the human body. Several of the ingredients, such as zinc and magnesium, are known to aid in boosting the immune system. Recurrent herpetic lesions have for some time been known to be associated with decreased immunity and/or compromised immune systems. The combined actions of the ingredients may thus act to aid an immune response. Some indications, such as the improved efficacy of the formulation when using the sulfate form of some of the ingredients as opposed to the oxide form, poses the speculation as to the efficacy of sulfur in the formulation. Although, the formulation utilizing the oxide form were effective, observation and patient reporting has led this clinician to speculate that the sulfate component may have a significantly beneficial action.

Example #8

BAKK. J—A 52 year old adult male with a history of herpetic lesions occurring every time he had prolonged exposure to the sunshine contacted my office with the request of attempting to prevent this from occurring at an upcoming social event at which he would be subjected to direct and prolonged sun exposure. From his past experience he knew without a doubt that a herpetic episode would be triggered. He wanted to avoid the pain and embarrassment.

Treatment: Patient was advised to take the average loading dosage for an adult male for 2 days prior to the anticipated exposure and then continue the same dosage for the two days of sun exposure. After which he was instructed to decrease to the average daily dosage for one week.

Follow-up: Patient complied with the above regimen and was elated in that he did not experience the expected herpetic episode. He stated that it was the first time he could remember not having an outbreak of the herpetic lesions with exposure to the sun.

The present invention has been described in an illustrative manner. It is to be understood that the terminology that has been used is intended to be in the nature of words of description rather than of limitation.

Many modifications and variations of the present invention are possible in light of the above teachings. Therefore, the present invention may be practiced other than as specifically described.

What is claimed is:

1. An orally ingested composition for the treatment of herpetic epidermal lesions caused by Herpes Simplex Virus (HSV-1), Herpes Zoster, and Herpes Genitalia, consisting essentially of:
    a) from 30 to 50 mg of zinc sulfate,
    b) from 5 to 25 mg of magnesium sulfate;
    c) from 15 to 60 mg of thiamin;
    d) from 15 to 30 mg of riboflavin;
    e) from about 4 to 12 mg of pyridoxine hydrochloride;
    f) from about 300 to 1000 mg of ascorbic acid;
    g) from 100 to 300 mg of niacin; and
    h) from about 20 to 70 mg of pantothenic acid;
wherein said composition is in the form of tablets or capsules.

2. An orally ingested composition as set forth in claim 1 wherein said composition is compounded into an ingestible form with an efficacious amount of titanium dioxide, talc, stearic acid, vegetable acetoglycerides, soybean oil, microcrystalline cellulose, and gelatin.

3. An orally ingested composition as set forth in claim 1 further including colorant and flavoring.

4. An orally ingested composition as set forth in claim 1 wherein varying load dosages are packaged in blister packages for delivery.

5. An orally ingested composition as set forth in claim 4 wherein the load dosage in a first blister package contains:
    a) from 30 to 50 mg of zinc sulfate;
    b) from 15 to 25 mg of magnesium sulfate;
    c) from 45 to 60 mg of thiamin;
    d) from 25 to 30 mg of riboflavin;
    e) from about 8 to 12 mg of pyridoxine hydrochloride;
    f) from about 900 to 1000 mg of ascorbic acid;
    g) from 270 to 300 mg of niacin; and
    h) from about 65 to 70 mg of pantothenic acid.

6. An orally ingested composition as set forth in claim 5 wherein the load dosage in a second and third blister package contains:
    i) from about 20 to 30 mg of zinc sulfate;
    j) from about 10 to 15 mg of magnesium sulfate;
    k) from about 30 to 40 mg of thiamin;
    l) from about 15 to 20 mg of riboflavin;
    m) from about 8 to 12 mg of pyridoxine hydrochloride;
    n) from about 600 to 1000 mg of ascorbic acid;
    o) from about 180 to 200 mg of niacin; and
    p) from about 40 to 65 mg of pantothenic acid.

7. An orally ingested composition as set forth in claim 6 wherein the load dosage in a fourth, fifth sixth and seventh blister package contains:
    q) from about 15 to 20 mg of zinc sulfate;
    r) from about 5 to 10 mg of magnesium sulfate;
    s) from about 15 to 20 mg of thiamin;
    t) from about 10 to 15 mg of riboflavin;
    u) from about 4 to 8 mg of pyridoxine hydrochloride;
    v) from about 300 to 600 mg of ascorbic acid;
    w) from about 90 to 180 mg of niacin; and
    x) from about 20 to 40 mg of pantothenic acid.

8. A treatment regimen method for the amelioration of Herpes Simplex Virus HSV-1, Herpes Zoster and Herpes Genitalia epidermal lesions, comprising administering to a patient in need thereof an oral daily regimen of a composition according to claim 1.

9. The treatment regimen as set forth in claim 8 wherein the composition is compounded into an ingestible form with an efficacious amount of pyridoxine hydrochloride, titanium dioxide, talc, stearic acid, vegetable acetoglycerides, soybean oil, and microcrystalline cellulose gelatin.

10. The treatment regimen as set forth in claim 2 wherein the composition includes a colorant and a flavoring.

11. The treatment regimen as set forth in claim 8 wherein said regimen includes ingesting varying loading dosages of the composition on a daily basis over a treatment period.

12. The treatment regimen as set forth in claim 11 wherein said regimen comprises ingesting on a first day:
    a) from 30 to 50 mg of zinc sulfate;
    b) from 15 to 25 mg of magnesium sulfate;
    c) from 45 to 60 mg of thiamin;
    d) from 25 to 30 mg of riboflavin;
    e) from about 8 to 12 mg of pyridoxine hydrochloride;
    f) from about 900 to 1000 mg of ascorbic acid;
    g) from 270 to 300 mg of niacin; and
    h) from about 65 to 70 mg of pantothenic acid.

13. The treatment regimen as set forth in claim 12 wherein said regimen further comprises ingesting on a second and third day:
    i) from about 20 to 30 mg of zinc sulfate;
    j) from about 10 to 15 mg of magnesium sulfate;
    k) from about 30 to 40 mg of thiamin;
    l) from about 15 to 20 mg of riboflavin;
    m) from about 8 to 12 mg of pyridoxine hydrochloride;
    n) from about 600 to 1000 mg of ascorbic acid;
    o) from about 180 to 200 mg of niacin; and
    p) from about 40 to 65 mg of pantothenic acid.

14. The treatment regimen as set forth in claim 13 wherein said regimen further comprises ingesting on a fourth through seventh day:
- q) from about 15 to 20 mg of zinc sulfate;
- r) from about 5 to 10 mg of magnesium sulfate;
- s) from about 15 to 20 mg of thiamin;
- t) from about 10 to 15 mg of riboflavin;
- u) from about 4 to 8 mg of pyridoxine hydrochloride;
- v) from about 300 to 600 mg of ascorbic acid;
- w) from about 90 to 180 mg of niacin; and
- x) from about 20 to 40 mg of pantothenic acid.

15. An orally ingested composition for the treatment of herpetic epidermal lesions caused by Herpes Simplex Virus (IISV-1), Herpes Zoster and Herpes Genitalia, consisting essentially of
- a) from 30 to 50 mg of zinc sulfate,
- b) from 5 to 25 mg of magnesium sulfate;
- c) from 15 to 60 mg of thiamin;
- d) from 15 to 30 mg of riboflavin;
- e) from about 4 to 12 mg of pyridoxine hydrochloride;
- f) from about 300 to 1000 mg of ascorbic acid;
- g) from 100 to 300 mg of niacin;
- h) from 50 to 70 mg of pantothenic acid; and
- i) about 500 mg of lysine;

wherein said composition further comprises an efficacious amount of an amino acid selected from the group consisting of taurine, L-methionine, L-glutamine, L-arginine, and L-carnitine; folic acid; selenium; copper; chromium; manganese and its sulfate; molybdenum; and an antioxidant and said composition is compounded into an ingestible tablet or capsule form with an efficacious amount of titanium dioxide, talc, stearic acid, vegetable acetoglycerides, soybean oil, microcrystalline cellulose, and gelatin.

* * * * *